United States Patent [19]

Evers

[11] 4,430,301
[45] Feb. 7, 1984

[54] APPARATUS FOR REMOVING A SAMPLE OF AT LEAST ONE PHASE FROM A MOVING MIXED PHASE

[75] Inventor: Heinz Evers, Linkenheim, Fed. Rep. of Germany

[73] Assignee: Wiederaufbereitungsanlage Karlsruhe Betriebsgesellschaft mbH, Eggenstein-Leopoldshafen, Fed. Rep. of Germany

[21] Appl. No.: 302,531

[22] Filed: Sep. 16, 1981

[30] Foreign Application Priority Data

Sep. 17, 1980 [DE] Fed. Rep. of Germany ....... 3034961

[51] Int. Cl.³ .............................................. B01D 11/00
[52] U.S. Cl. .................................. 422/119; 422/257; 210/511
[58] Field of Search ................. 210/511, 522, DIG. 5, 210/794, 802; 422/256, 257, 101, 119

[56] References Cited

U.S. PATENT DOCUMENTS

| | | | |
|---|---|---|---|
| 1,488,947 | 4/1924 | Smith | 422/119 X |
| 2,034,281 | 3/1936 | Buchholz | 422/119 X |
| 2,214,248 | 9/1940 | Hawley | 210/DIG. 5 |
| 2,662,001 | 12/1953 | Burns et al. | 422/257 |
| 2,746,846 | 5/1956 | Grunewald et al. | 422/257 X |
| 3,204,934 | 9/1965 | Graham et al. | 422/256 X |
| 3,613,889 | 10/1971 | Reed | 210/802 |
| 3,718,257 | 2/1973 | Bach | 210/802 |
| 3,768,648 | 10/1973 | Anderson et al. | 210/802 |
| 4,251,378 | 2/1981 | Simone et al. | 210/522 |

FOREIGN PATENT DOCUMENTS 1502561 3/1978 United Kingdom ............... 422/256

*Primary Examiner*—Frank A. Spear, Jr.
*Attorney, Agent, or Firm*—Spencer & Frank

[57] ABSTRACT

Apparatus for extracting a dispersed phase from a moving mixed phase which contains two substantially mutually insoluble liquids of different densities which form a dispersed phase and a continuous phase. The apparatus includes a pipe passing through the wall separating the mixed phase from its environment and having a funnel-shaped end which projects into the mixed phase and has a conical, inner wall. The funnel-shaped end presents an opening for capture of the dispersed phase, with the funnel shaped end being oriented such that the width or diameter of the opening is at right angles to the direction of movement of the dispersed phase.

9 Claims, 2 Drawing Figures

APPARATUS FOR REMOVING A SAMPLE OF AT LEAST ONE PHASE FROM A MOVING MIXED PHASE

BACKGROUND OF THE INVENTION

The present invention relates to an apparatus for removing a sample of at least one phase from a moving mixed phase consisting of two liquids which have different densities and which are substantially mutually insoluble, and which form a dispersed phase and a continuous phase.

In many chemical processes operating with liquids, particularly in liquid-liquid countercurrent extraction processes, it is necessary, for reasons of process control or control of the desired operating states, to take samples. In such a process, two liquids which are insoluble or hardly soluble in one another may be moved or transported in a pipe or column. If these liquids are mixed for process reasons, the taking of a sample has in the past been effected, for example, by extracting the mixed phase from the pipe or column by means of a sampling tube or sample taking system as provided by Professor Hartland, ETH, Zurich. If the mixing of the liquids is effected for reasons of transferring substances from one liquid to the other, transfers of the substance cannot be prevented from taking place during the time when the mixed phase has been extracted from the column, but separation of the two liquid phases has not yet taken place. During the subsequent analytical examination of the substance concentrations in the liquids, errors up to 100% may then occur.

The sample taking system according to Professor Hartland, which essentially comprises a metal cylinder with a Teflon cap containing a perforated screen, makes it possible only to extract the lighter phase from the moving mixed phase. The extraction rate, however, must be kept low, at less than 1 ml per minute, since at higher rates the heavier phase would be extracted as well. This is particularly unsuitable if the light phase is the dispersed phase and the heavy phase is the continuous phase.

Another disadvantage of the prior art devices is the possibility of clogging of the fine bores at the sample taker input and in the soiling or covering of the surface of the material of the sample taker, which is specific for each phase, after long periods of operation. This results in a reduction of separation of the extracted liquid. A further disadvantage, in the case of a pulsating liquid-liquid countercurrent extraction column, is the effect of the pulsation on the hydraulic conditions in the sample taker. Moreover, the relatively complicated structure of the sample taking system according to Professor Hartland and the difficult cleaning connected therewith, which is done, for instance, with compressed air for which efficiency is not always assured, is a further disadvantage.

SUMMARY OF THE INVENTION

It is an object of the present invention to provide a device for extracting a sample of at least one phase from a moving mixed phase formed of two substantially mutually insoluble liquids having different densities, one liquid forming the dispersed phase and the other liquid forming the continuous phase, with the device being able to collect the dispersed phase, and/or the continuous phase retain it, and discharge it during extraction as quickly as possible and free from the other phase.

It is another object of the present invention to provide an extraction device for the above-identified purpose which is not sensitive to surface coatings.

It is another object of the present invention to provide an extraction device with which changes in column conditions, such as a change in the proportion of the dispersed phase with respect to the total volume of the two liquids, changes in the cross section of the perforated bottoms, or changes in the pulse level and frequency, will not have an adverse effect on the extraction of a sample.

It is another object of the present invention to provide an extraction device which is universally applicable, and which may be used to take samples of both light and heavy phases.

It is another object of the present invention to provide an extraction device which is operable as described hereinabove, under various hydraulic states, in, for example, a column.

It is a further object of the present invention to provide an extraction device, which, for reasons of process control, is capable of extracting the dispersed phase and/or the continuous phase at a rate of 10 to 20 ml per minute.

To achieve these objects, and in accordance with its purpose, the present invention provides an apparatus for extracting a sample of at least one phase from a moving mixed phase containing two countercurrent flowing substantially mutually insoluble liquids of different densities which form a dispersed phase and a continuous phase. The apparatus includes at least one pipe, which passes through the wall separating the mixed phase from its environment, and is (are each) provided with a funnel-shaped end having a conical, inner wall. The funnel shaped end extends into the mixed phase so as to present an opening for capture of only one phase, the dispersed phase or the continuous phase respectively, and is disposed or oriented on the pipe such that the diameter or width of this opening is at right angles to the direction of movement of the counercurrent phases, i.e., the dispersed phase and the continuous phase, respectively. Generally, the moving mixed phase will be contained in a walled transporting means such as a column. The pipe (pipes) of the apparatus then passes (pass) through the wall of the transporting means i.e. the column wall which separates the mixed phase from its environment.

In an advantageous embodiment of the present invention, the width of the capture opening lies in a range between twice the drop diameter of the dispersed phase, and one third the width of the mixed phase measured transverse to the direction of movement of the mixed phase.

DETAILED DESCRIPTION OF THE PREFERRED EMBODIMENTS

Figure 1:
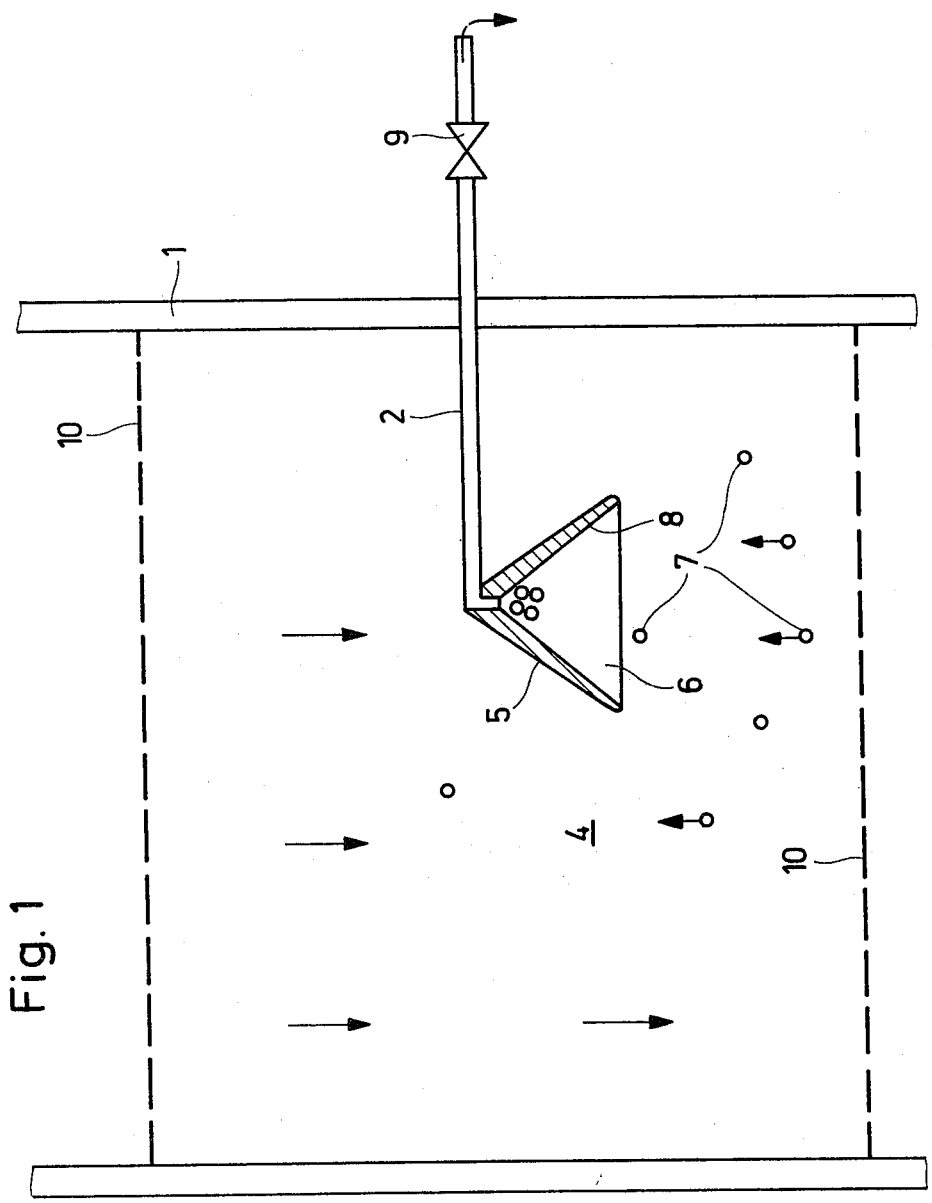
FIGS. 1 and 2 are schematic, longitudinal, cross-sectional views of a column containing an extraction apparatus according to the present invention with FIG. 1 showing an apparatus for extracting samples of one phase of the mixed phase and FIG. 2 showing an apparatus for separately extracting samples of both phase of the mixed phase.

FIG. 1 shows a screen or perforated bottom column section comprising the column wall 1, upper and lower perforated or screen bottoms 10 and an extraction or discharge device according to the invention which is disposed between the two perforated bottoms 10. This device essentially includes a pipe 2 which passes through the column wall 1, into the inner space of the column in which the mixed phase 4 is located and through which the continuous phase is flowing downwardly in the direction of the arrows and the dispersed phase is flowing in the opposite direction. The pipe 2 has an end in the shape of a funnel 5 provided with a capture opening 6. The end or funnel 5 is oriented on the pipe 2 such that the width or plane of capture opening 6, i.e., the cross-sectional plane of the funnel 5, faces and is at a right angle to the direction of movement or flow of the dispersed phase 7, when the pipe 2 is installed in its operating position. In the illustrated embodiment, the pipe 2 extends perpendicular to the wall 1 and the funnel 5 forms a right angle with the longitudinal axis of the pipe 2.

The end or funnel 5 of the pipe 2 catches or captures the upward flowing dispersed phase 7 out of mixed phase 4 and, due to the physical characteristics of the dispersed phase 7, causes the dispersed phase 7 to be collected in pipe 2 and at the conical wall 8 of the funnel 5. The continuous phase is displaced out of the funnel 5 during the collection of the dispersed phase 7. Preferably, the width or diameter of the capture opening 6 is in the range between twice the drop diameter of the dispersed phase 7 and one third of the width of the mixed phase 4 measured transverse to the direction of flow of the continuous phase and to the direction of flow of the dispersed phase. The diameter of the pipe 2 is selected with consideration of the desired extraction rate and the given flow rates of the both phases which are mixed in the column. The apparatus according to the invention can be designed to be replaceable from the exterior of the column. Pipe 2 is provided with a conventional discharge valve 9, suitable for use with liquids, located outside of the column wall 1.

With the device according to the FIG. 1, it is possible to extract either a dispersed lighter phase or a dispersed heavier phase. Where a dispersed lighter phase is to be extracted, as shown in the FIG. 1, the funnel 5 is oriented such that its capture opening 6 faces downward toward the dispersed phase 7 which rises in the column. In the case where the heavier phase constitutes the dispersed phase, the heavier phase can be extracted by orienting the apparatus so that the capture opening 6 of the funnel 5 faces upward toward the descending dispersed phase.

The height of the funnel should be not more than 60% of the distance between the perforated bottoms 10. The distance of the funnel to the lower or to the upper perforated bottom 10 should be at least 10 to 20% of the distance between the two perforated bottoms.

The opening angle of the funnel should be in the range between 60° and 90°. The diameter of the pipe 2 should be as small as possible. Normally it is between 2 and 4 mm. The quantity of the taken sample should be not more than 60% of the quantity of the dispersed phase which arrives at the opening area 6 of the funnel 5.

EXAMPLE

In a column 100 mm in width and a perforate bottom distance of 50 mm with a free area of 23% (diameter of the holes 4.5 mm), a funnel of 25 mm diameter and 30 mm in height was used. The material of the funnel was stainless steel. The continuous phase was aqueous 3 M $HNO_3$, the dispersed countercurrent organic phase was 30% TBP/Kerosene. The flow rates of both phases (org.: aqu. = 1:1) were in the range of 200 l/h up to 1000 l/h. The hold up changes between 3 and 35%. The pipe 2 of the funnel consists also of stainless steel. The pipe diameter was 4 mm, the free width was 2 mm. The sample was taken with a velocity of 5 ml/min. up to 20 ml/min.

Result

There was no continuous phase in the taken organic phase sample.

Figure 2:
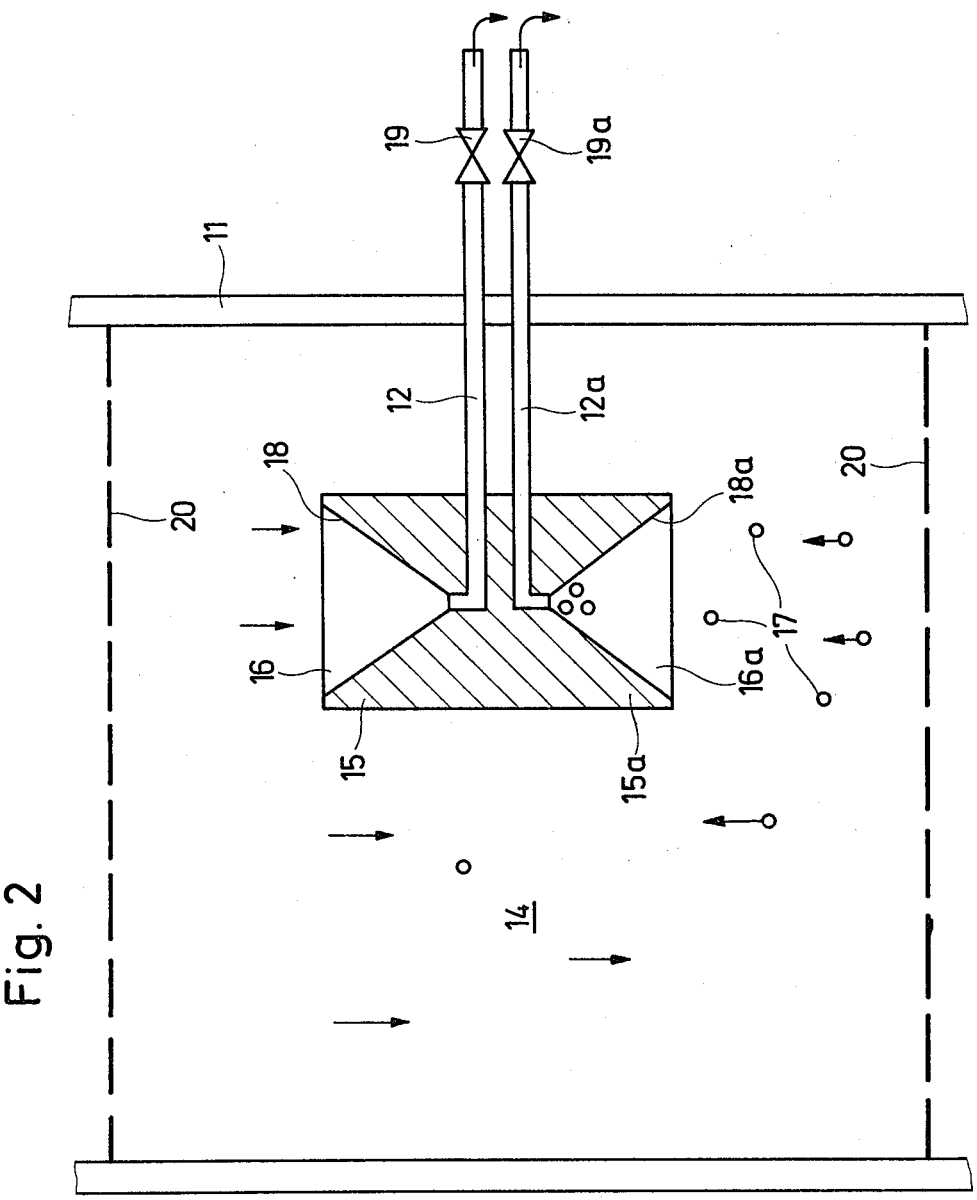

FIG. 2 shows also a screen or perforated bottom column section comprising the column wall 11, upper and lower perforated or screen bottoms 20 and an extraction or discharge device according to the invention which is disposed between the two perforated bottoms 20. This device essentially includes two pipes 12, 12a which pass through the column wall 11, into the inner space of the column in which the mixed phase 14 is located and through which the continuous phase is flowing downwardly in the direction of the arrows and the dispersed phase is flowing in the opposite direction. The pipe 12 has an end in the shape of a funnel 15 provided with a capture opening 16. In the same manner the pipe 12a has an end in the shape of an other funnel 15a provided with a capture opening 16a. The funnels 15 and 15a are arranged in the inner space of the column corresponding to the arrangement of funnel 5 in FIG. 1, but in opposite direction one to the other, so that the plane of the capture opening 16 faces and is at a right angle to the direction of movement or downward flow of the continuous phase, and that the plane of the capture opening 16a faces and is at a right angle to the direction of movement or upward flow of the dispersed phase 17.

The funnel 15 a catches or captures the upward flowing dispersed phase 17 out of the mixed phase 14 and the funnel 15 catches or captures the downward flowing continuous phase. The continuous phase is displaced out of the funnel 15a, and the dispersed phase 17 is displaced out of the funnel 15. The diameter of the pipes 12 and 12a are selected with consideration of the desired extraction rate and the given flow rates of the both phases which are mixed in the column. The apparatus according to the invention can be designed to be replaceable from the exterior of the column. Pipes 12 and 12a are provided with conventional discharge valves 19 and 19a respectively, suitable for use with liquids, located outside of the column wall 11.

The present invention is advantageous in that the dispersed phase need not, as in the Hartland system, penetrate an opposing screen-like surface, but rather, is openly collected in a depository and stablizes itself due to the existing physical relationships. The apparatus is also of simple design, which results in savings during manufacture, and is easy to clean. Moreover, the apparatus of the present invention makes it possible to take larger sample quantities in a relatively short period of time, for example, about 20 ml per minute with about a 3% hold-up in the column. In view of the simple structural design, a surface coating during longer periods of inactivity can no longer have an adverse influence on the sample quality. In the rest state, during which no samples are being extracted, the collected phase is adjusted to the phase concentration presently in the column by the arrival of new drops in the depository.

Depending on the operating medium, the apparatus according to the invention, including pipe 2 (12, 12a) with funnel 5 (15, 15a) is produced from a material having the appropriate resistance to the operating medium, such as stainless steel or an appropriate plastic material.

It will be understood that the above description of the present invention is susceptible to various modifications, changes and adaptations and the same are intended to be comprehended within the meaning and range of equivalents of the appended claims.

What is claimed is:

1. An extraction apparatus for extracting a sample of at least one phase from a mixed phase moving through a walled transporting means with said mixed phase comprising two substantially mutually insoluble liquids of different densities which are moving in opposite directions in the transporting means and which form a dispersed phase and a continuous phase which are countercurrent to one another, said apparatus comprising: at least one pipe which passes through the wall of the transporting means and has a funnel-shaped end having a conical inner wall, said funnel-shaped end projecting into the mixed phase and presenting an opening for capture of only one of the dispersed and continuous phases, and said funnel-shaped end is oriented in the mixed phase such that the width of its said opening is at right angles to the direction of movement of the two countercurrent phases and faces in the direction of movement of the one of the two countercurrent phases to be extracted.

2. The apparatus defined in claim 1 wherein said opening of said funnel shaped end has a width in a range between twice the diameter of the drops of the dispersed phase and one-third of the width of the mixed phase, measured transverse to the direction of movement of the mixed phase.

3. The apparatus defined in claim 1 or 2, wherein said funnel shaped end is oriented in the mixed phase such that its said opening faces in the direction of movement of the dispersed phase.

4. The apparatus defined in claim 1 or 2, wherein said funnel shaped end is oriented in the mixed phase such that its said opening faces in the direction of movement of the continuous phase.

5. The apparatus defined in claim 1 further comprising a discharge valve connected to said pipe and located outside of the transporting means.

6. The apparatus defined in claim 1 wherein the transporting means comprises a column section having two perforated bottoms placed at right angles to the direction of movement of the mixed phase, one of the bottoms being located upstream of said apparatus, and one of the bottoms being located downstream of said apparatus, with reference to the direction of movement of the mixed phase.

7. The apparatus defined in claim 6 wherein said funnel-shaped end has a height which is not greater than 60% of the distance between said perforated bottoms.

8. The apparatus defined in claim 7 wherein the distance between said opening of said funnel-shaped end and the facing said perforated bottom is at least 10–20% of the distance between said perforated bottoms.

9. The apparatus as defined in claim 1 further comprising a further one of said pipes which passes through the wall of the transporting means and which has a funnel-shaped end with an opening for capture of one of the countercurrent phases, said funnel-shaped end of said further pipe being oriented in the mixed phase such that the width of its said opening is at right angles to the direction of movement of the two countercurrent phases and faces in the direction of movement of the other of the two countercurrent phases, whereby samples of both of the two countercurrent phases may be separately extracted from the mixed phase.

* * * * *